(12) United States Patent
Poore et al.

(10) Patent No.: US 7,536,227 B1
(45) Date of Patent: May 19, 2009

(54) SHIELDED ELECTRODE FOR NERVE SENSING

(75) Inventors: John W. Poore, South Pasadena, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 53 days.

(21) Appl. No.: 11/045,626

(22) Filed: Jan. 26, 2005

(51) Int. Cl.
A61N 1/05 (2006.01)
A61N 5/04 (2006.01)

(52) U.S. Cl. ........................... 607/118; 600/377

(58) Field of Classification Search ......... 607/115–118, 607/1–3, 44–46, 48–49; 600/372–373, 377–378, 600/381, 345, 26–28, 386–393, 546–548
See application file for complete search history.

(56) References Cited

U.S. PATENT DOCUMENTS

| | | | | |
|---|---|---|---|---|
| 4,341,221 | A * | 7/1982 | Testerman | 600/377 |
| 4,750,499 | A * | 6/1988 | Hoffer | 607/116 |
| 4,940,065 | A * | 7/1990 | Tanagho et al. | 607/118 |
| 5,031,621 | A * | 7/1991 | Grandjean et al. | 600/377 |
| 5,111,815 | A * | 5/1992 | Mower | 607/4 |
| 5,215,089 | A * | 6/1993 | Baker, Jr. | 600/377 |
| 5,487,756 | A * | 1/1996 | Kallesoe et al. | 607/118 |
| 5,658,318 | A | 8/1997 | Stroetmann et al. | 607/6 |
| 5,824,027 | A * | 10/1998 | Hoffer et al. | 607/118 |
| 5,919,220 | A * | 7/1999 | Stieglitz et al. | 607/118 |
| 5,964,702 | A * | 10/1999 | Grill et al. | 600/377 |
| 6,292,703 | B1 * | 9/2001 | Meier et al. | 607/118 |
| 6,587,725 | B1 * | 7/2003 | Durand et al. | 607/42 |
| 6,600,956 | B2 * | 7/2003 | Maschino et al. | 607/118 |
| 6,666,821 | B2 * | 12/2003 | Keimel | 600/365 |
| 7,006,875 | B1 * | 2/2006 | Kuzma et al. | 607/118 |
| 2002/0193697 | A1 * | 12/2002 | Cho et al. | 600/529 |
| 2003/0074039 | A1 * | 4/2003 | Puskas | 607/118 |

(Continued)

FOREIGN PATENT DOCUMENTS

WO     WO 03/035165 A1     5/2003

(Continued)

OTHER PUBLICATIONS

Lotte N. S. Andreasen, Johannes J. Struijk, Artefact Reduction with Alternative Cuff Configurations, Oct. 2003, IEEE Transactions on Biomedical Engineering, vol. 50, 1160-1165.*

(Continued)

*Primary Examiner*—Carl H Layno
*Assistant Examiner*—Jessica Reidel

(57) ABSTRACT

A shielded electrode assembly for nerve sensing is disclosed. The electrode assembly is a flexible and generally tubular structure that can be wrapped around and secured to the outer surface of a nerve so as to establish and maintain electrical contact therewith. The assembly includes an electrically conductive shield with conductive reference electrodes positioned at opposite ends thereof to define an isopotential reference. A sense electrode is placed within the isopotential reference and senses signals either with respect to the isopotential reference or to a sense reference electrode also positioned within the isopotential reference to a sensing device. The isopotential reference provides a region along which nerve activity propagating along the nerve can be sensed with a large attenuation of any external noise which may be present adjacent the sensing region of the nerve. The shielded electrode assembly facilitates direct, long-term nerve sensing with reduced need for filtering or signal processing.

17 Claims, 6 Drawing Sheets

U.S. PATENT DOCUMENTS

| | | | |
|---|---|---|---|
| 2003/0078643 A1* | 4/2003 | Schulman et al. | 607/116 |
| 2003/0083716 A1 | 5/2003 | Nicolelis et al. | 607/45 |
| 2003/0144710 A1* | 7/2003 | Haugland et al. | 607/48 |
| 2003/0153954 A1* | 8/2003 | Park et al. | 607/17 |
| 2004/0024439 A1* | 2/2004 | Riso | 607/117 |
| 2004/0210261 A1* | 10/2004 | King et al. | 607/9 |
| 2005/0010265 A1* | 1/2005 | Baru Fassio et al. | 607/48 |

OTHER PUBLICATIONS

M. Haugland, "A flexible method for fabrication of nerve cuff elec\-trodes," Proc. IEEE EMBS 18th Int. Ann. Conf., pp. 359-360, 1996.*

* cited by examiner

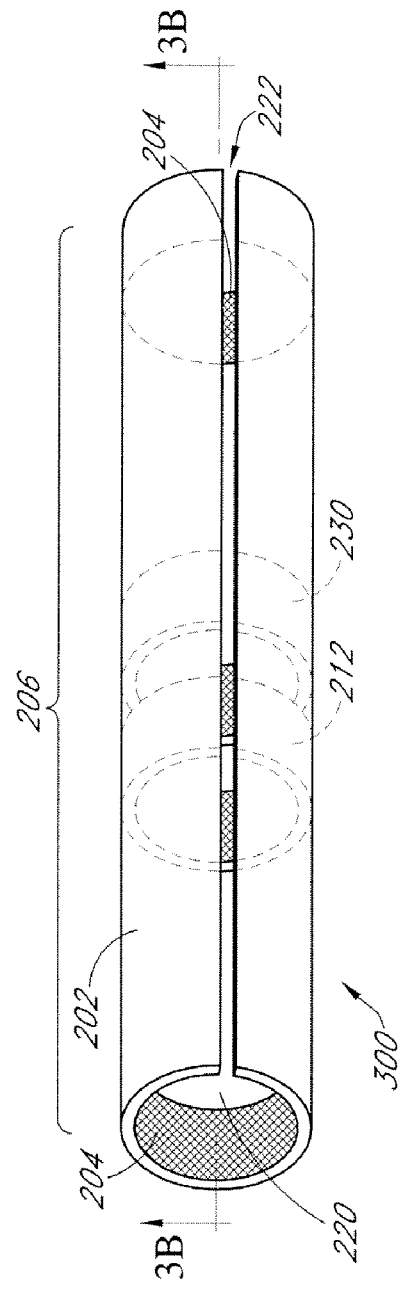
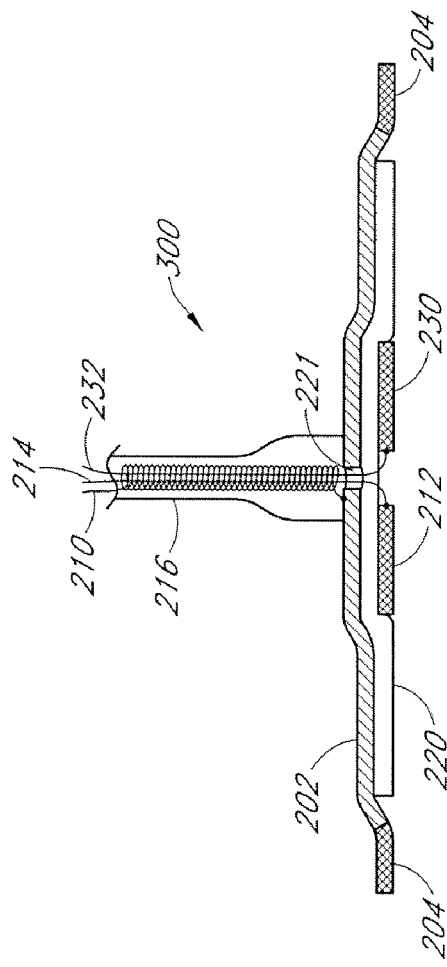
FIG. 3A
FIG. 3B

SHIELDED ELECTRODE FOR NERVE SENSING

FIELD OF THE INVENTION

The invention relates to the field of implantable medical devices and, in particular, to shielded electrodes for in vivo nerve sensing, such as of the vagus or phrenic nerve, and to implantable medical devices employing such electrodes.

BACKGROUND

A variety of devices and methods are known for internally sensing physiological activity and providing therapeutic stimulation for a variety of data gathering and therapeutic purposes. For example, implantable stimulation devices are known that automatically internally sense one or more of the patient's physiological parameters and selectively provide stimulation to nerve tissue as therapy, such as for epileptic conditions, pain treatment, or apnea.

Implantable medical devices which internally sense electrical signals indicative of physiological processes of the patient have typically done so by placing one or more sense electrodes in contact with the associated patient tissue. These electrodes are then connected to appropriate amplifier and/or filter circuits such that the sensed physiologically generated electrical signals are conducted and transformed into a format suitable for analysis and utilization, such as for determination of therapy delivery or clinical data analysis.

Peripheral nerves of the body, such as the vagus or phrenic nerves, offer enticing possibilities for internally measuring the activity of these or other nerves for a variety of possible uses. For example, the phrenic nerve conducts signals originating in the brain to the diaphragm to induce the diaphragm to contract resulting in an inspiration phase of the patient's cyclic respiration. Thus, the ability to directly sense activity on the phrenic nerve would provide information indicative of the inherent perceived respiration demand rather than inferential information related to respiratory demand, such as systemic $CO_2$ concentration, or to the respiratory response, such as a minute volume measurement. Direct sensing of phrenic nerve activity would also provide the ability to diagnose a central sleep apnea (CSA) condition by directly observing the lack of or reduced phrenic nerve activity.

However, such direct nerve sensing, particularly on a chronic or long-term basis, has been inhibited by several factors. A major impediment to direct nerve sensing in the body is accurately discriminating the nerve signals from background electrical signals also present in the patient's body. Nerve activity, such as on the phrenic nerve, typically is of microvolt to fractional microvolt in amplitude and of approximately 300 to 10 kilohertz in frequency. Background "noise", also present within the patient's body adjacent nerves of interest, is typically several orders of magnitude greater, e.g. in the millivolt range, and of comparable frequency spectra. This background noise can arise from the patient's cardiac activity, muscular activity, and conducted electrical signals induced from background electromagnetic energy, such as electrical line supply at 60/50 Hz.

As the background signal noise can be thousands of times greater in amplitude and covering a comparable frequency range to the signal of interest, e.g. nerve activity, it is a significant technical challenge to accurately isolate the nerve activity of interest from the background noise. It is known to surgically expose nerve tissue; distance the nerve from other patient tissue thus isolating a portion of the nerve from conducted noise; attach sensing electrodes to the nerve; and sense signals directly from the nerve with appropriate amplifier and filter circuits. However, such open, invasive procedures are obviously not practical on a long-term basis.

Methods and procedures are known which might be adapted for at least somewhat effectively isolating a nerve signal from background noise, however they are typically highly demanding of processor speed and power. For example, a sensed signal can be digitized and processed with a variety of digital signal processing (DSP) algorithms. However, such DSP algorithms typically are far too demanding of processor capability and power consumption than is admissible within the available processing bandwidth and limited battery capacity of an implantable device. Filtering offers limited assistance as the frequency spectra of nerve signals is comparable to that of the background noise.

Thus it will be appreciated that there is a demand for accurate reliable direct sensing of nerve activity which is suitable for long-term chronic use, such as by a battery powered implantable medical device. There is also a need for a device which can accurately sense low level signals in an environment with relatively high amplitude noise of comparable frequency spectra and provide these signals in a manner for effective use which does not overburden the available processing bandwidth or power consumption available to a battery powered implantable medical device. It would be further advantageous to provide a sensing system which facilitates implantation by the clinician and the flexibility for application to multiple nerves.

SUMMARY

Preferred embodiments include an implantable shielded electrode assembly that isolates a sense electrode from external noise to allow the electrode to directly sense nerve activity in spite of a relatively high level of background noise. In one implementation, the shielded electrode assembly encases a portion of the nerve with an electrically conductive shield that is partially in contact with opposed outer surfaces of the nerve so as to define an isopotential reference region. In this implementation, the sense electrode is positioned within this isopotential reference region such that the sense electrode senses a relatively clean signal of the nerve activity propagated along the nerve. The shielded electrode assembly provides the ability for long-term direct nerve sensing with reduced need for signal processing which makes the shielded electrode assembly attractive for use in implantable medical devices operating from batteries of limited capacity and with processors of limited available processing bandwidth.

One embodiment comprises an electrode assembly for sensing nerve signals, the electrode assembly comprising an implantable shield assembly configured to contact a nerve so as to define a substantially isopotential reference and at least one implantable sense electrode configured to contact the nerve and positioned with respect to the shield assembly such that the sense electrode is at least partially shielded by the shield assembly from potentials arising externally to the nerve.

Another embodiment comprises an implantable medical device comprising a processor and a shielded electrode assembly in communication with the processor and configured to be secured to a nerve wherein the electrode assembly senses nerve activity in a manner that is at least partially shielded from electrical potentials arising external to the nerve.

Yet another embodiment comprises a sensing system for nerve sensing comprising implantable means for sensing nerve signals and implantable means for shielding arranged with respect to the means for sensing such that the means for shielding provides a low resistance path for electrical potentials external to the nerve such that the means for sensing is at least partially shielded from the external potentials. These and other objects and advantages of the invention will become more apparent from the following description taken in conjunction with the accompanying drawings.

BRIEF DESCRIPTION OF THE DRAWINGS

FIGS. 3A and 3B illustrate another embodiment of a shielded electrode for nerve sensing in perspective and side section views respectively;

DETAILED DESCRIPTION

The following description includes the best mode presently contemplated for practicing the invention. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Figure 1B:
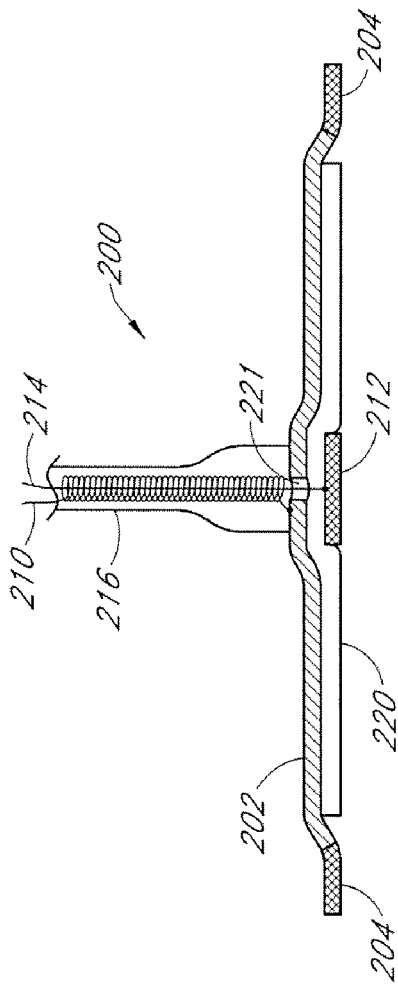
FIG. 1B is a side section view of one embodiment of a shielded electrode for nerve sensing.
Figure 1A:
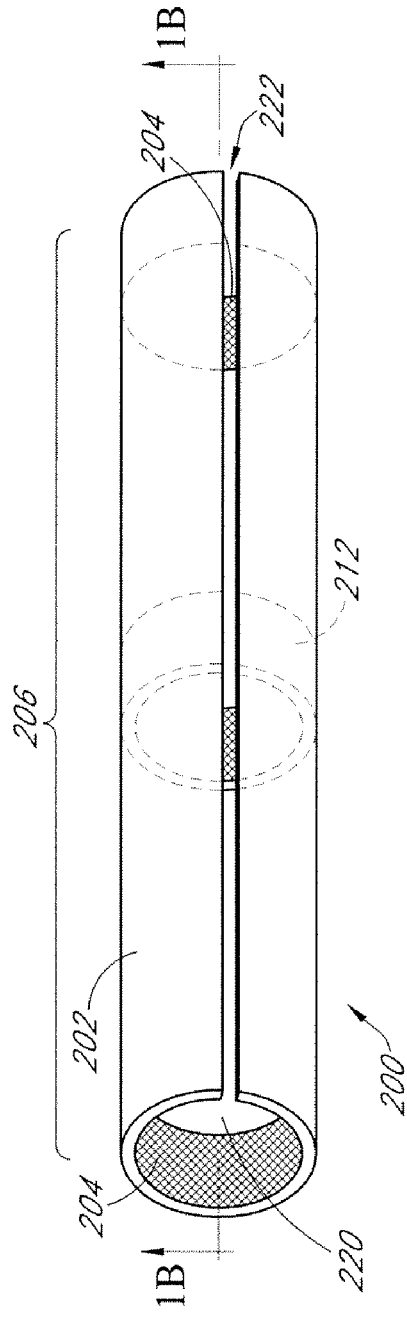
FIG. 1A is a perspective partial view of one embodiment of a shielded electrode for nerve.

FIG. 1 illustrates in perspective and cross section one embodiment of a shielded electrode assembly 200. The shielded electrode assembly is configured to be readily attached to a nerve 224 (FIG. 2) to directly sense nerve activity on the nerve 224 while providing improved isolation from external noise which may be present within the patient's body.

It will be appreciated that as used herein "noise" refers simply to electrical signals which may be present but are preferably isolated, at least to some extent, from sensing as performed by the shielded electrode assembly 200 to thereby improve the sensing. Thus, noise can refer to electrical signals not of interest such as electromagnetic radiation, line voltages, and muscle artifacts as well as signals, such as electrical signals arising from cardiac activity which are of interest to a higher level system employing the shielded electrode assembly 200. "Isolation", "isolating", "shielded", and "shielding" refer to an attenuation of the noise with respect to the sensing which, in preferred embodiments, can be substantial, but is not necessarily absolute. "Sensing" of "signals" refers to monitoring representative characteristics of one or more physiological processes which in various embodiments can comprise the voltage, current, frequency, and/or morphology characteristics of electrical signals as well as other physical characteristics such as pressure, temperature, pH, partial gas pressure, etc. that, in certain embodiments, are transformed into corresponding electrical signals.

The shielded electrode assembly 200 of this embodiment is a generally flexible tubular structure that is formed of malleable or resilient materials and includes an opening or slit 222 such that the shielded electrode assembly 200 can be splayed open and wrapped around a nerve 224 so as to be in contact therewith. When comprising resilient or elastic materials, the configuration, size, thickness, and elastic nature of the materials of the shielded electrode assembly 200 are preferably selected such that the shielded electrode assembly 200 can resiliently bear upon the outer surface of the nerve 224 so as to establish and maintain a good electrical contact therewith, however in such a manner as to not exert undue pressure thereto so as to avoid injury to or impairment of function of the nerve 224.

In this embodiment, the shielded electrode assembly 200 comprises a shield assembly 202 defining a generally central tubular portion of the shielded electrode assembly 200 as well as reference electrodes 204 positioned at opposite ends and extending circumferentially about inner surfaces of the shield assembly 202. Both the shield assembly 202 and reference electrodes 204 preferably comprise conductive and biocompatible materials. Suitable electrically conductive and biocompatible materials can include gold or platinum filled silicone rubber or polyurethane as well as a mesh of biocompatible conductive metal such as platinum or gold. The shield assembly 202 and/or reference electrodes 204 can also comprise a continuous foil of conductive and biocompatible material in particular embodiments.

In this embodiment, the reference electrodes 204 are preferably configured to contact a substantially circumferential surface about a region of the nerve 224 so as to achieve a good electrical contact therewith. The reference electrodes 204 each substantially circumferentially contact separated portions of the nerve 224 and are each electrically connected to the shield assembly 202 which also substantially circumferentially encases the portion of the nerve 224 positioned between the opposed reference electrodes 204. Thus, as the shield assembly 202 and reference electrodes 204 comprise an electrically conductive generally cylindrical structure substantially encasing a portion of the nerve 224, a substantially isopotential reference region 206 is defined within which region the nerve 224 is more electrically isolated from external noise which may be present within the patient's body. Incident electrical signals impinging upon the nerve 224 in the isopotential reference region 206 are provided with a relatively low resistance circuit path and are at least partially shunted through the shield assembly 202 and reference electrodes 204.

The shielded electrode assembly 200 of this embodiment also comprises a shield lead 210 which is electrically connected to the shield assembly 202 and thus to the reference electrodes 204 and which extends away from the shield assembly 202 and reference electrodes 204 to provide a reference based on the isopotential reference 206 created by the shield assembly 202 and reference electrodes 204.

The shielded electrode assembly 200 of this embodiment also comprises a sense electrode 212 which is connected to a sense lead 214 extending away from the sense electrode 212 and preferably positioned alongside the shield lead 210. The sense electrode 212 also preferably comprises electrically conductive and biocompatible materials such as the gold or platinum filled silicone rubber or polyurethane, mesh, or foil material previously described as suitable for use with the shield assembly 202 and reference electrode 204. The selection of the materials comprising the shield assembly 202, the reference electrodes 204, and the sense electrodes 212 are preferably selected to be of like materials to mitigate galvanic effects when implanted within a patient. In certain embodiments, the shielded electrode assembly 200 can additionally or alternatively comprise one or more shunts to mitigate galvanic effects as well as possible AC coupling. The sense electrode 212 is, in this embodiment, configured as an annular cuff extending substantially circumferentially about a surface of the nerve 224 and is positioned intermediate the opposed reference electrodes 204.

The shielded electrode assembly 200 also comprises an insulation element 220 which is positioned between the sense electrode 212 and the shield assembly 202 and reference electrodes 204. The insulation element 220 also extends between the opposed reference electrodes 204 as well as extending substantially circumferentially about the nerve 224 so as to electrically isolate the sense electrode 212 from the shield assembly 202 and reference electrodes 204 as well as limiting electrical contact of the shield electrode assembly 200 and the outer surface of the nerve 224 to the opposed reference electrodes 204 and the intermediately disposed sense electrode 212 so as to facilitate sensing within the isopotential reference 206.

Thus, the shielded electrode assembly 200 creates an isopotential reference 206 defined by the interconnected electrically conductive reference electrodes 204 and shield assembly 202 which substantially circumferentially contact separated annular outer surfaces of the nerve 224 and, thus provides greater electrical isolation for the intermediate portion of the nerve 224 enclosed within the shielded electrode assembly 200 from external electrical noise.

As the sense electrode 212 is positioned within this isopotential reference 206, electrical signals passing along the nerve 224 can be readily sensed by the sense electrode 212 with reference to the isopotential reference 206 while providing improved isolation for this sensing from external noise which may be present within the patient's body. Thus, relatively high magnitude electrical noise, such as arising from cardiac activity, muscular activity, or conducted or radiated electromagnetic energy is more effectively isolated thus allowing the shielded electrode assembly 200 to readily sense relatively small magnitude electrical signals of interest, such as activity on the nerve 224, which may be several orders of magnitude lower in amplitude than the background noise and of comparable frequencies. A relatively clean signal can be sensed from the nerve 224, thus reducing the need for filtering or signal processing to evaluate the sensed activity of the nerve 224.

As can be seen in FIG. 1, the insulation element 220 comprises an opening 221 through which the sense lead 214 can pass. The sense lead 214 and shield lead 210 are encased within an insulative and biocompatible lead cover 216 which also extends away from the shield assembly 202, reference electrode 204 and sense electrode 212 so as to allow the sense lead 214 and shield lead 210 to conduct sensed activity of the nerve 224 distally for further analysis and use.

Figure 2:
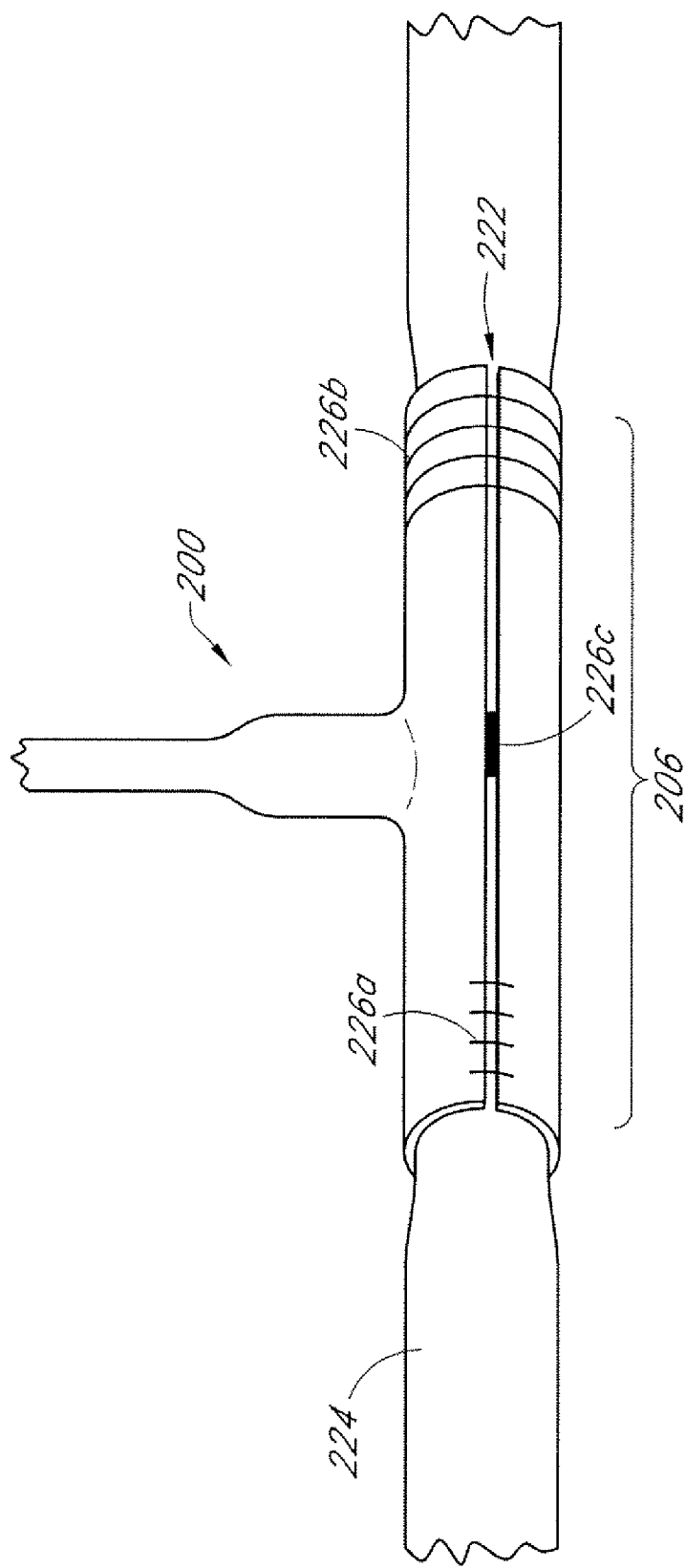
FIG. 2 illustrates one embodiment of a shielded electrode affixed to a nerve for sensing signals propagated on the nerve.

FIG. 2 illustrates one embodiment of a shielded electrode assembly 200 as secured to a patient's nerve 224. In this embodiment, the shielded electrode assembly 200 has been splayed open and extended around the nerve 224 and released so as to substantially wrap around the nerve 224. In this embodiment, securements 226 are provided to further secure the shielded electrode assembly 200 in place about the nerve 224. In various embodiments, this can comprise securements illustrated as securements 226a, 226b, 226c which may be provided individually or in combination.

Securements 226a comprise sutures joining opposed edges of the shielded electrode assembly and secured so as to draw the opposed edges together into adjacency or abutment. Securements 226b comprise sutures wrapping circumferentially about the exterior surface of the shielded electrode assembly 200 similarly so as to draw the opposed edges of the shielded electrode assembly 200 into adjacency or abutment. Securements 226c comprise a bio-compatible adhesive which may also be electrically conductive and applied along the opposed edges of the opening or slit 222 to secure the opposed edges of the shield electrode assembly 200 together. As previously mentioned, the application of the securement(s) 226 as well as the material construction and physical dimensioning of the shielded electrode assembly 200 is preferably selected to maintain secure electrical contact with the outer surface of the nerve 224 but to avoid excessive application of pressure to the nerve 224 to avoid injury to or impairment of the function of the nerve 224, particularly when implanted in the patient for long-term use. It will be appreciated that a variety of sizes and configurations of shielded electrode assembly 200 may be provided to accommodate the requirements of specific applications.

FIG. 3 illustrates another embodiment of a shielded electrode assembly 300. The shielded electrode assembly 300 shares several components and structures substantially similar to those previously described for the shielded electrode assembly 200 and similar reference designators will be used and descriptions of the similar components will not be repeated. The shielded electrode assembly 300 comprises the shield assembly 202 and reference electrodes 204 together defining an isopotential reference 206, the shield lead 210, sense electrode 212, sense lead 214, lead cover 216, insulation element 220 having an opening 221 and slit 222, and securements 226 substantially as previously described.

The shielded electrode assembly 300 also comprises a sense reference electrode 230 which is connected to a sense reference lead 232. The sense reference electrode 230 is substantially similar in material and construction to the sense electrode 212 and, in this embodiment, both the sense electrode 212 and sense reference electrode 230 are positioned so as to be in substantially circumferential contact with separated portions of the patient's nerve 224 and also positioned within the isopotential reference 206.

Thus, in this embodiment, electrical signals propagating along the nerve 224 are better shielded within the isopotential reference 206 from external noise which may be present within the patient's body and this nerve 224 activity can be sensed by the sense electrode 212 with reference to the sense reference electrode 230 as well as optionally with reference to the reference electrodes 204 as for the shielded electrode assembly 200. Also, by evaluating the relative timing/potential differences of signals sensed between the sense electrode 212 and sense reference electrode 230, the direction of propagation of the signals along the nerve 224 can be determined.

It will be appreciated that in other embodiments, a plurality of sense electrodes 212 and sense reference electrodes 230 and corresponding sense leads 214 and sense reference leads 232 can be provided within a single shielded electrode assembly 300 to effectively provide multiple sensing pairs, triplets, etc. or that multiple sense electrodes 212 and/or sense reference electrodes 230 can be electrically coupled in alternative embodiments of shielded electrode assemblies 200, 300.

Thus the shielded electrode assemblies 200, 300 provide the ability to be implanted on a long-term basis within a patient and to provide direct nerve sensing which is substantially shielded from external noise, particularly noise of greater amplitude and of similar frequency spectra. This facilitates direct nerve sensing while reducing the need for filtering or signal processing which is highly demanding of processing and power supply capabilities. Thus, the shielded electrode assemblies 200, 300 readily enable implantable medical devices, such as implantable cardiac stimulation devices, to directly monitor nerve activity for better evaluation of the patient's condition as well as to more effectively enable the devices to deliver therapy when indicated, such as to mitigate episodes of central sleep apnea (CSA) or to more accurately track therapeutic pacing to the patient's metabolic demand.

Figure 4:
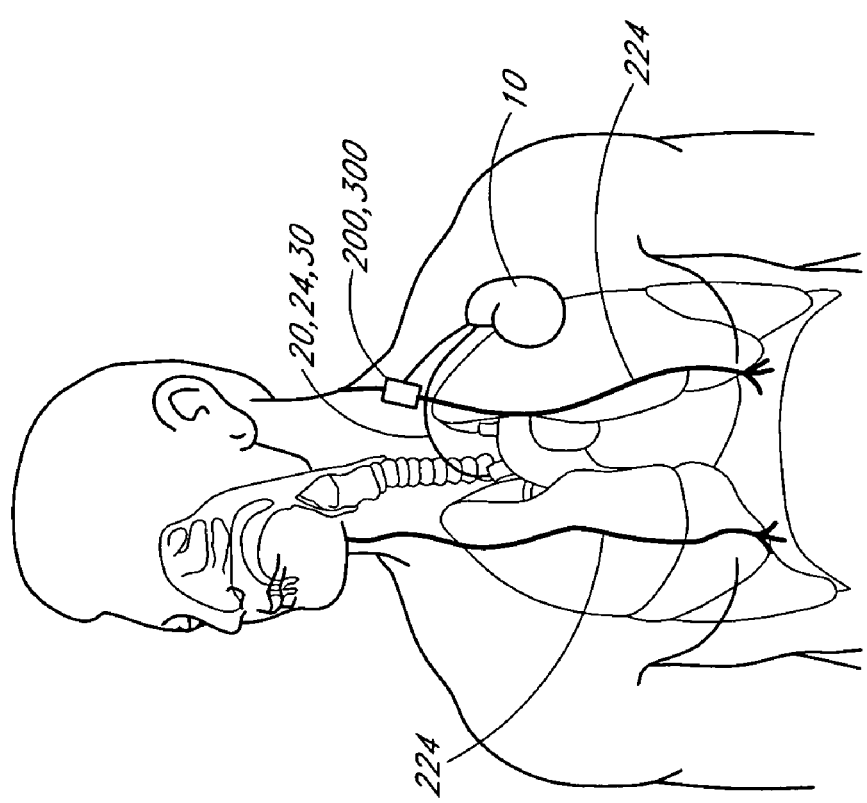
FIG. 4 illustrates embodiments of a shielded electrode affixed to an implantee's phrenic nerve and in communication with an implantable medical device.

FIG. 4 illustrates one embodiment of use of a shielded electrode assembly 200, 300 in concert with an implantable cardiac stimulation device 10 to sense a nerve 224. In this embodiment, the shielded electrode assembly 200, 300 is applied to the patient's phrenic nerve 224 to sense phrenic nerve activity. Thus, signals sensed on the phrenic nerve 224 can be conducted by the shield lead 210 and/or sense reference lead 232 and sense lead 214 to the implantable cardiac stimulation device 10 to provide information to the device 10 relating to directly sensed activity on the phrenic nerve 224.

Figure 5:
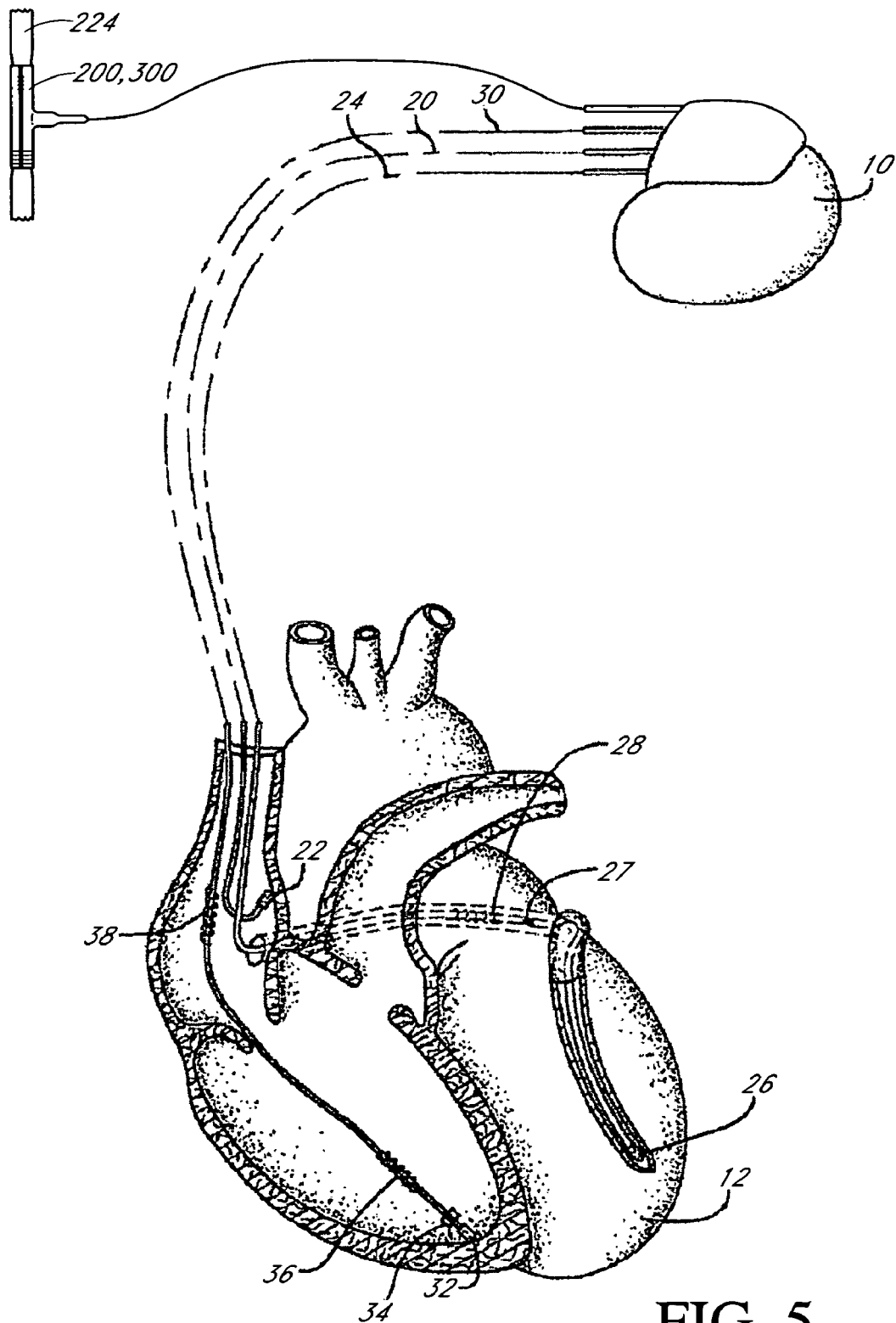
FIG. 5 is a simplified diagram illustrating an implantable stimulation device in electrical communication with at least three leads implanted into a patient's heart for delivering multi-chamber stimulation and shock therapy as well with a nerve.

As shown in greater detail in FIG. 5, one or more of the shielded electrode assemblies 200, 300 is applied to corresponding nerve(s) 224, such as the phrenic and/or vagus nerves, and is further connected to the device 10. The implantable stimulation device 10, referred to hereafter as "device 10" for brevity, is also in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 6:
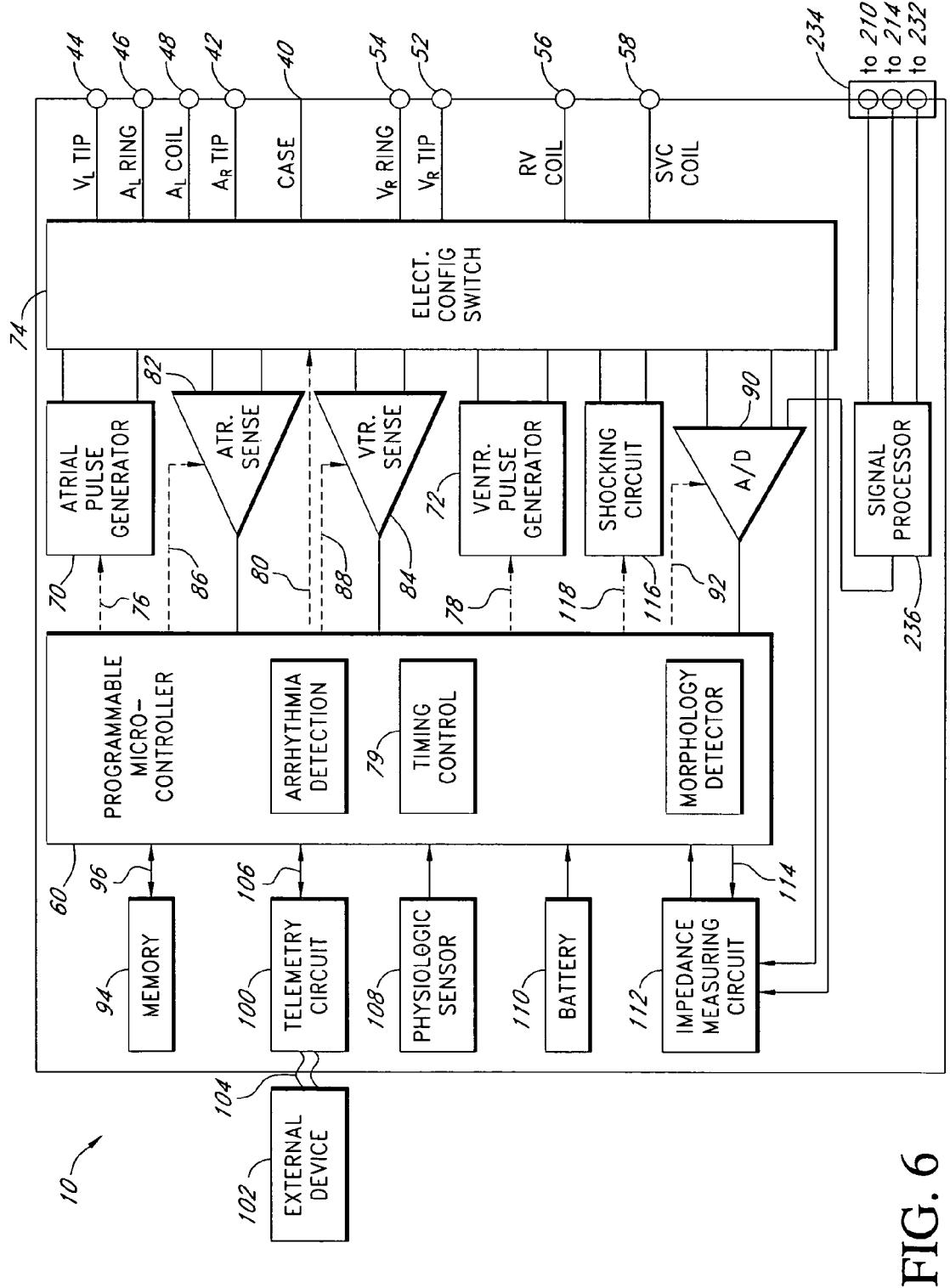
FIG. 6 is a functional block diagram of a multi-chamber implantable stimulation device illustrating the basic elements of a stimulation device which can provide cardioversion, defibrillation and pacing stimulation in four chambers of the heart as well as direct nerve sensing.

As illustrated in FIG. 6, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

A housing 40 for the stimulation device 10, shown schematically in FIG. 6, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM and/or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 6, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102, which, in certain embodiments, comprises a programmer. The data acquisition system 90 is coupled to the right atrial lead 20, the coronary sinus lead 24, and the right ventricular lead 30 through the switch 74 to sample cardiac signals across any pair of desired electrodes.

In one embodiment, the device 10 also comprises at least one connector 234 configured for connection to the shield lead 210, sense lead 214, and sense reference lead 232 of the shielded electrode assemblies 200, 300. Nerve signals from the shield lead 210, sense lead 214, and sense reference lead 232 are further received by a signal processor 236. The signal processor 236 includes appropriate input impedance and buffering characteristics and, in certain embodiments, also amplifies or otherwise conditions nerve signals received from the shield lead 210, sense lead 214, and sense reference lead 232. The output of the signal processor 236 is provided to the data acquisition system 90 which further processes the nerve signals and provides them to the microcontroller 60. In other embodiments, nerve signals are provided directly from the one or more connectors 234 to the data acquisition system 90.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, desired operating parameters or other programming instructions of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 may be activated from a standby condition in response to an indication from a radio frequency (RF) detector (not shown) that signals of a predetermined strength are being received. The telemetry circuit 100 can communicate with the microcontroller 60 via a communication link 106.

The telemetry circuit 100 also advantageously allows intracardiac electrograms and status information relating to the operation of the device 10 (as contained in the microcontroller 60 or memory 94) to be sent to the external device 102 through an established communication link 104 as well as data from sensors 108. In certain embodiments, data from the sensors 108 is selectively sent continuously via the communication link 104 and, in alternative embodiments, the data from the sensors 108 is sent in frames and/or as a derived signal, e.g. an average or rate.

The device 10 comprises one or more physiologic sensor(s) 108, commonly referred to as a "rate-responsive" sensor, because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

While shown in FIG. 6 as being included internal to the stimulation device 10, it is to be understood that the sensors 108 may also be positioned outside and in communication with the stimulation device 10 and may include a variety of sensors 108 some or all of which may be external to the device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, ventricular gradient, etc. It is also to be understood, that in certain embodiments, the sensors 108 are capable of sensing multiple parameters and providing all the sensed parameters or a selected number of the parameters to the device 10.

In certain embodiments, the sensors 108 comprise one or more of the shielded electrode assemblies 200, 300 as previously described such that the shielded electrode assemblies 200, 300 in combination with the device 10 define a sensing system. In these embodiments, the shielded electrode assemblies 200, 300 provide signals to the device 10 corresponding to sensed activity of one or more corresponding nerves 224. Thus, the device 10 can receive signals from the shielded electrodes assemblies 200, 300 which are relatively "clean" carrying a significantly reduced level of background noise and which the device 10 can thus utilize with significantly reduced need for filtering or signal processing. The device 10 can store the signals sensed in the onboard memory 94 and/or provide the signals telemetrically to the external device 102 as previously described for further evaluation/utilization.

The device 10 can also use the sensed signals internally to evaluate the patient's condition, such as for determination of appropriate therapy delivery. In one embodiment, the shielded electrode assembly(ies) 200, 300 provides signals to the device 10 corresponding to sensed activity on the patient's phrenic nerve 224. In these embodiments, the device 10 is provided with signals corresponding directly to the patient's respiratory demand as indicated by phrenic nerve activity.

The device 10 can evaluate these sensed nerve activity signals with measurements of the patient's respiratory response, such as obtained by a sensor 108 configured as an impedance sensor which is arranged to measure the patient's transthoracic impedance. As the transthoracic impedance varies with the amount of air in the patient's lungs through the inhalation and expiration of the patient's breathing, the sensor 108 can determine the depth and rate of the patient's respiration in a known manner to determine a minute ventilation measure of the respiratory output of the patient. Thus, in one embodiment, the shielded electrode assemblies 200, 300 can provide an additional indication of the patient's respiration to the device 10 to more accurately track therapeutic cardiac pacing to the patient's metabolic demand in a rate responsive manner.

The shielded electrode assemblies 200, 300 can also provide signals to the device 10 to indicate delivery of therapy related to other physiological aspects. In one embodiment, the device 10 receives signals corresponding to phrenic nerve 224 activity that may indicate an absence or reduction in phrenic nerve 224 activity that may correspond to an episode of CSA. In these embodiments, the device 10 can then initiate an overdrive pacing therapy to treat the CSA and/or can provide direct stimulation to the phrenic nerve 224 to restore respiration. In a similar manner, the shielded electrode assemblies 200, 300 can provide signals to the device 10 corresponding to activity of the vagus nerve 224 to induce the device 10 to provide therapeutic stimulation related to the activity of the vagus nerve 224.

The stimulation device additionally includes a battery 110 which provides operating power to all of the circuits shown in FIG. 6. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected.

As further shown in FIG. 6, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the invention and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes and, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An electrode assembly for sensing nerve signals, the electrode assembly comprising:

an electrically conductive layer adapted to form an implantable shield assembly, extending circumferentially around at least a first portion of a nerve;

at least two reference electrodes electrically coupled to the shield assembly and extending circumferentially around the first portion of the nerve wherein the shield assembly and the reference electrodes are configured to contact a nerve so as to define a substantially isopotential reference; and at least one implantable sense electrode configured to contact the nerve and positioned between the conductive layer of the shield assembly and the first portion of the nerve such that the sense electrode is electrically insulated from the shield assembly and at least partially shielded by the shield assembly from potentials arising externally to the nerve.

2. The electrode assembly of claim 1, wherein the reference electrodes are further configured to substantially circumferentially contact outer surfaces of the nerve and wherein the reference electrodes are connected at opposite ends to the shield assembly so as to define the isopotential reference as a generally cylindrical region bounded by the shield assembly and the one or more reference electrodes.

3. The electrode assembly of claim 1 further comprising a sense reference electrode configured to contact the nerve and positioned with respect to the shield assembly such that the sense reference electrode is also at least partially shielded by the shield assembly from potentials arising externally to the nerve such that the sense and sense reference electrode can sense signals propagated along the nerve with reduced influence of external electrical noise.

4. The electrode assembly of claim 1, further comprising:
a shield lead connected to the shield assembly; and
a sense lead connected to the sense electrode wherein the shield lead and sense lead are electrically insulated from each other and extend outwards from the shield assembly and sense electrode.

5. The electrode assembly of claim 1, wherein the electrode assembly is at least partly flexible and is configured such that the electrode assembly is wrappable about the nerve so as to extend substantially circumferentially about the outer surface of the nerve.

6. The electrode assembly of claim 5, further comprising securements securing the electrode assembly in place on the nerve.

7. The electrode assembly of claim 6, wherein the securements comprise sutures.

8. An implantable medical device comprising:
a processor; and
a shielded electrode assembly in communication with the processor, wherein the shielded electrode assembly comprises an implantable shield assembly having an electrically conductive layer extending circumferentially around at least a first portion of a nerve and at least two reference electrodes electrically coupled to the shield assembly and extending circumferentially around the first portion of a nerve wherein the shield assembly and the reference electrodes are configured to contact a nerve so as to define a substantially isopotential reference and at least one sense electrode which is electrically insulated from the shield assembly and positioned between the electrically conductive layer of the shield assembly and the first portion of the nerve and wherein the electrode assembly senses nerve activity in a manner that is at least partially shielded from electrical potentials arising external to the nerve.

9. The implantable medical device of claim 8, wherein the shielded electrode assembly further comprises:
at least one sense electrode configured to contact the nerve and positioned with respect to the shield assembly such that the sense electrode is shielded by the shield assembly from potentials arising externally to the nerve.

10. The implantable medical device of claim 9, further comprising a lead assembly conducting signals sensed by the sense electrode to the processor.

11. The implantable medical device of claim 8, further comprising:
a stimulation pulse generator; and
at least one implantable stimulation lead with at least one stimulation electrode configured to contact patient tissue such that the device can selectively provide therapeutic stimulation to the patient.

12. The implantable medical device of claim 11, wherein the device evaluates signals received from the shielded electrode assembly and delivers therapy based at least in part on the evaluation.

13. The implantable medical device of claim 12, wherein the shielded electrode assembly is configured to contact the phrenic nerve and wherein the device evaluates signals received from the shielded electrode assembly for indications of central sleep apnea and, upon determination that an episode of central sleep apnea has occurred, initiates a therapeutic treatment.

14. The implantable medical device of claim 13, wherein the therapeutic treatment comprises enabling an overdrive pacing regimen.

15. The implantable medical device of claim 8, further comprising at least one physiological sensor which senses at least one physiological parameter independently from the shielded electrode assembly.

16. The implantable medical device of claim 8, further comprising memory wherein the device stores data received from the shielded electrode assembly.

17. The implantable medical device of claim 8, further comprising a telemetry circuit such that the device can telemetrically transmit data relating to signals sensed by the shielded electrode assembly to an external device.

* * * * *